June 9, 1936. W. B. MURRAY Plant Pat. 181
HYBRID TEA ROSE
Filed Jan. 30, 1936
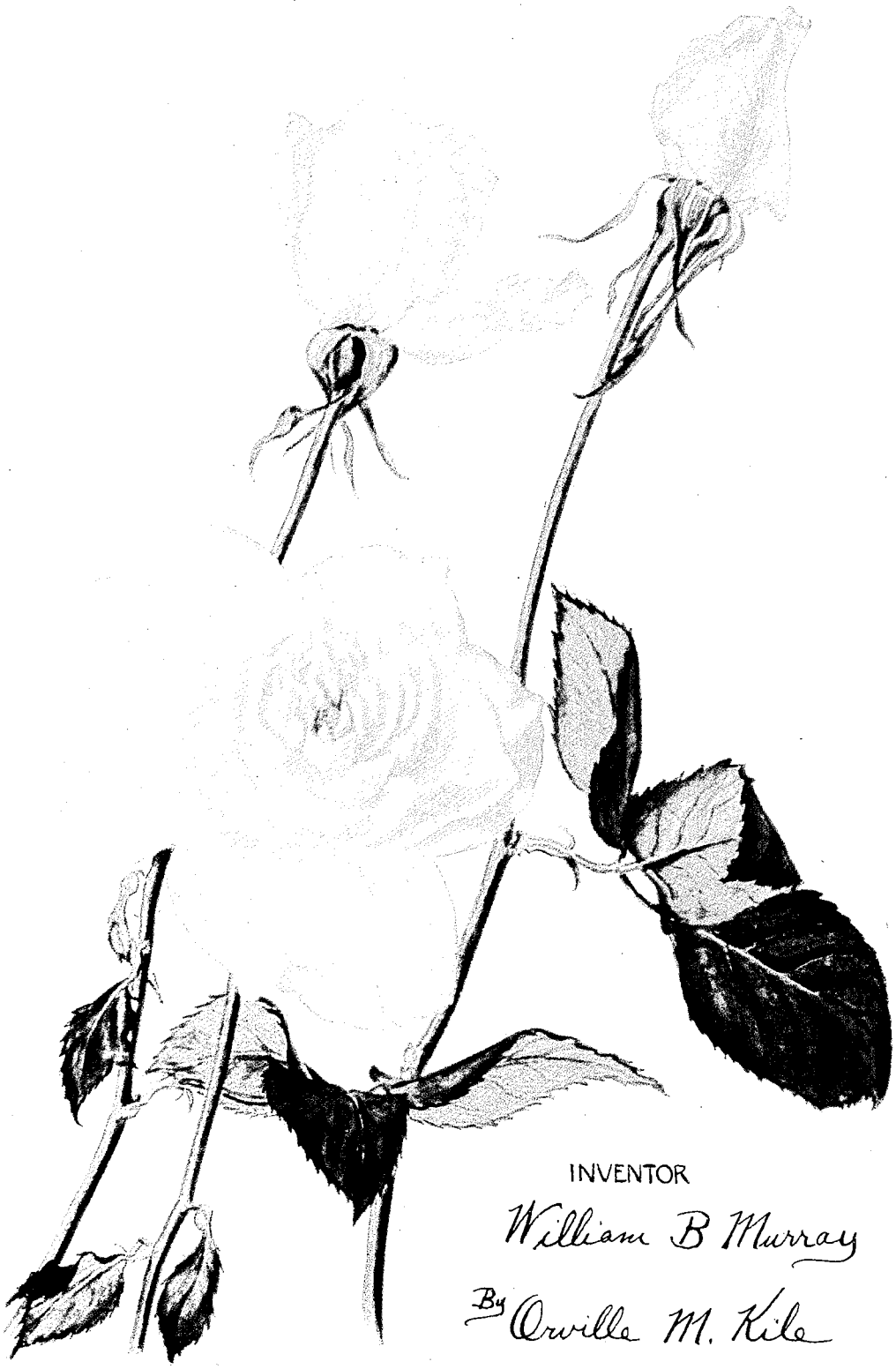
INVENTOR
William B Murray
By Orville M. Kile
PLANT PATENT AGENT Patented June 9, 1936

UNITED STATES PATENT OFFICE

181

HYBRID TEA ROSE

William B. Murray, Atco, N. J.

Application January 30, 1936, Serial No. 61,580

1 Claim. (Cl. 47—61)

My new variety is a sport of the well known variety Briarcliff. Since discovering this sport I have carefully nurtured and observed it and through numerous asexual reproductions covering several generations I have proved its desirable qualities to be definite and fixed.

The accompanying illustrations show a bud just beginning to open, another half opened, and a blossom in its prime, as well as foliage and stems. These illustrations show this new variety of rose in approximately full size (in the original paintings) and in as near the natural coloring as possible. It must be understood, however, that there will be a certain amount of color tone variation between different specimens.

The illustrations and descriptions are based on greenhouse specimens grown in the vicinity of Philadelphia in late January.

*The plant*

The plant is of moderate size, being normally about 4 feet high and of rather bushy growth. An average specimen will produce 25 to 30 flowers per season. My new variety is more resistant to disease than is Briarcliff.

*Foliage.*—Moderate in quantity.

*Leaves.*—Compound, usually 3 to 5 leaflets, latter being medium-sized rather than large, flat rather than waved. A typical terminal leaflet measures 2¾ inches long by 1¾ inches wide, being relatively wide for the length. Rather finely serrate; veining not prominent; texture not heavy. Upper surface semi-glossy; color "Forest Green" (Plate XVII, Ridgway's Color Standards and Nomenclature). The under surface has a notable brownish-red tinge, which color is also prominent on the nether side of the midrib. This color is most notable on the newer growth. (In the illustration several leaves are curved in order to show the color of the under side).

*Rachises.*—Straight with an occasional very small thorn or large spine found on the nether surface.

*Petioles.*—The petioles of the leaflets are extremely short, often not more than $\frac{1}{32}$ of an inch and rarely more than $\frac{1}{16}$.

*Stipules.*—Medium size and only slightly inclined to the foliaceous form. Points in most specimens are sharp but non-curling and in the occasional specimen where the points are not sharp the recurving or back curling is slight.

*Stems.*—Straight, medium stout, "Apple Green" in color; entirely free from thorns until the fifth leaf or eye below the blossom is reached.

*The flower*

*The bud.*—Pointed and of medium size. As it begins to open, the bud becomes somewhat urn-shaped.

*Sepals.*—Turn back even before the bud begins to open.

*Color.*—Color of the bud is only slightly darker than in the opening flower (see below).

The blossom:

*Size.*—Large, measuring 4½ to 5 inches across.

*Form.*—Cup shaped, though showing a somewhat pointed center the first day after the bud begins to open. The sex organs are not exposed because of the large number of small central petals.

*Petalage.*—The petals in January number about 25 large outer, 20 medium and 15 small. Since the first 4 or 5 rows of petals are large and the central petals of fair size and all of medium texture, this makes a large, heavy flower—much larger than Briarcliff. In the fully opened flower the petal arrangement is imbricated. The petals are flat rather than crinkled or waved and are not inclined to recurve much. Only a slight point is found at the top of midline of each petal—no ragged appearance.

*Color.*—Rather uniform, but upper surface of petals slightly darker shade than reverse. Distribution of color over surface of individual petals uniform except for small light (almost white) area at base of each petal. The darker shades toward the center of the flower are "Rose Color" (Plate XII, Ridgway's Color Standards and Nomenclature). The lighter shades, notable principally on the outer rows of petals and as the flower ages, are "Deep Rose Pink" fading to "Rose Pink" (Plate XII, Ridgway's). The color has a certain luminous quality difficult to portray. The light to white area at the base of each petal is quite small, in fact scarcely noticeable except at the stage of opening in some specimens where the central pointed effect is retained for a few hours or a day and the outer row of petals has continued to turn back. In this small white area only the faintest suggestion of yellow is found. Faint green veining is visible in the white area on the inside surface of the petals but this is scarcely visible on the outside surface. In the final stages the petals take on a purplish color.

*Persistence.*—Petals are retained fairly well, moderate lasting qualities.

*Fragrance.*—Pleasantly and moderately fragrant.

*Sepals.*—Simple rather than foliaceous. Many specimens show one of the five sepals with a small leaf-like development, but the remaining four sepals are simple. On most specimens the sepals would be described as short and simple.

*Hips.*—Narrow and disproportionately long.

*Peduncle.*—Straight, medium heavy, and smooth, having no visible spines but occasional rudimentary spine can be felt; color "Apple Green" (Plate XVII).

*Stamens.*—Medium number, slender, white; bear small buff colored anthers.

*Pistils.*—Medium number; white with slightly yellowish tips.

*Comparisons*

In general color effect this new variety is similar to Briarcliff and Briarcliff Brilliance. But there are numerous differences not only in plant and flower structure but in color as well, which plainly distinguish this new variety. The following are some of the more notable differences.

1. Briarcliff has numerous thorns on the flower stems, while my new variety has none.

2. The stipules of Briarcliff are wide and have long curling points; my new variety shows far less tendency to foliaceous stipule growth.

3. The sepals of Briarcliff are notably foliaceous while those of my new variety are short and simple.

4. The leaves of Briarcliff are wavy and deeply serrated, while in my new variety the leaves are flat and rather finely serrated; moreover the leaves of my variety show a brownish-red tinge on their nether sides, which is absent in Briarcliff.

5. My new variety produces a larger and heavier blossom than either Briarcliff or Briarcliff Brilliance. This results partly from the somewhat larger number of petals, their heavier texture, and the larger size of the individual petals. The petals of my new variety are more regular in form, not having the crinkled effect nor the prominently pointed and cut petals of Briarcliff or Briarcliff Brilliance.

6. The color of each petal is more uniform in my new variety, there being less tendency toward lighter areas in the central portions of the petals. There is less yellow tint at the base of the petals in my new variety.

Having thus disclosed my invention, I claim:

The variety of hybrid tea rose plant herein described and illustrated, characterized particularly by its lack of thorns on the flowering shoots, and other peculiarities of foliage as described, as well as by its large and heavy blossoms of a uniform rose to rose pink color.

WILLIAM B. MURRAY.